(12) United States Patent
Tomisaki et al.

(10) Patent No.: US 8,983,159 B2
(45) Date of Patent: Mar. 17, 2015

(54) MAMMOGRAPHY APPARATUS, IMAGE PROCESSING APPARATUS, AND IMAGE PROCESSING METHOD

(75) Inventors: Takayuki Tomisaki, Otawara (JP); Naoko Kuratomi, Sakura (JP); Kae Ohnuki, Yokohama (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 797 days.

(21) Appl. No.: 12/825,639

(22) Filed: Jun. 29, 2010

(65) Prior Publication Data

US 2011/0002519 A1    Jan. 6, 2011

(30) Foreign Application Priority Data

Jul. 2, 2009 (JP) ................. 2009-157872

(51) Int. Cl.
| | | |
|---|---|---|
| G06T 7/00 | (2006.01) | |
| A61B 6/00 | (2006.01) | |
| A61B 6/12 | (2006.01) | |
| G06T 5/00 | (2006.01) | |
| G06T 5/40 | (2006.01) | |
| H04N 5/243 | (2006.01) | |
| H04N 5/32 | (2006.01) | |

(52) U.S. Cl.
CPC . *A61B 6/461* (2013.01); *A61B 6/12* (2013.01); *A61B 6/4233* (2013.01); *A61B 6/502* (2013.01); *G06T 5/008* (2013.01); *G06T 5/40* (2013.01); *H04N 5/243* (2013.01); *H04N 5/32* (2013.01); *A61B 6/469* (2013.01); *G06T 2207/10081* (2013.01); *G06T 2207/20012* (2013.01); *G06T 2207/30068* (2013.01)
USPC ........................................... 382/131

(58) Field of Classification Search
CPC .......................................... A61B 6/461
IPC .......................................... A61B 6/461
See application file for complete search history.

(56) References Cited

U.S. PATENT DOCUMENTS

| | | | | |
|---|---|---|---|---|
| 6,956,975 | B2 * | 10/2005 | Young .......................... | 382/263 |
| 8,160,346 | B2 * | 4/2012 | Gatesoupe et al. ........... | 382/132 |
| 2008/0002872 | A1 | 1/2008 | Gatesoupe et al. | |

FOREIGN PATENT DOCUMENTS

| | | |
|---|---|---|
| JP | 2002-330953 A | 11/2002 |
| JP | 2007-068852 A | 3/2007 |
| JP | 2009-116581 A | 5/2009 |

OTHER PUBLICATIONS

Japanese Office Action with English Translation for Japanese Patent Application No. 2009-157872 mailed on Sep. 3, 2013.

* cited by examiner

*Primary Examiner* — Michelle L Le
(74) *Attorney, Agent, or Firm* — Yoshida & Associates, LLC (57) ABSTRACT

A mammography apparatus has a determination unit, a setting unit, a generating unit and a display unit. The determination unit determines whether a radiographic image of a breast contains an implant part based on a pixel value distribution in a predetermined region concerning data of the radiographic image. The setting unit changes a setting of a parameter for a tone conversion process based on a determination made by the determination unit. The generating unit generates a display image based on the radiographic image by application of the parameter. The display unit displays the display image.

17 Claims, 8 Drawing Sheets

MAMMOGRAPHY APPARATUS, IMAGE PROCESSING APPARATUS, AND IMAGE PROCESSING METHOD

CROSS-REFERENCE TO RELATED APPLICATION

This application is based upon and claims the benefit of priority from Japanese Patent Application No. 2009-157872, filed on Jun. 2, 2009, the entire contents of which are incorporated herein by reference.

FIELD

Present embodiments described herein relates generally to a mammography apparatus, an image processing apparatus and an image processing method which set a parameter for an auto window function based on a radiographic image, generate display images based on the set parameters, and displays the generated display images.

BACKGROUND

Mammography is widely used to provide a two-dimensional image of breast tissue for breast examinations in diagnosing cancer or other abnormalities. The breasts, which have a delicate three-dimensional structure, are radiographed using a special X-ray apparatus.

Typical X-ray apparatuses use intense (hard) X-rays to expose bones and other hard objects. On the other hand, X-ray apparatuses used for breast examinations handle soft tissue such as fat and mammary glands, and thus use weak (soft) X-rays. At the same time, since the breast examination is the only examination in which skin comes into direct contact with a machine of the X-ray apparatus, various precautions are taken.

The mammography apparatus takes radiographs by pulling and compressing the breast. Radiographs are taken, for example, in two directions: in MLO (mediolateral-oblique) and CC (cranial-caudal) views.

When a radiographic image is initially displayed, a conventional mammography apparatus finds a maximum pixel value and a minimum pixel value in the radiographic image and set a center pixel value between the maximum pixel value and the minimum pixel value as a window level. The apparatus performs this calculation automatically (auto window function) and presents a display image based on the radiographic image. Also, regardless of the presence or absence of an implant (silicon pack) in the breast, the auto window function of the conventional mammography apparatus calculates a cumulative frequency beginning with the minimum pixel value using pixel values of the radiographic image and sets the pixel value at which the cumulative frequency reaches a predetermined threshold (e.g., 10% of the total) as the minimum pixel value.

The auto window function is disclosed by, for example, a medical diagnostic imaging apparatus which automatically calculates a maximum pixel value, minimum pixel value, and window level appropriate for a region which needs to be examined.

However, with the auto window function of the conventional mammography apparatus, if a radiographic image contains an implant part (a portion showing an implant), a proportion of the implant part in the radiographic image is large and pixel values of the implant part are relatively small. Thus, a histogram of a radiographic image containing the implant part has a peak on a low-pixel-value side, causing a cumulative frequency calculated starting from the low-pixel-value side to shift greatly to the low-pixel-value side when compared to a histogram of a radiographic image not containing the implant part. Consequently, with the auto window function of the conventional mammography apparatus, the display image based on a radiographic image becomes generally dark, resulting in a window in which the mammary gland and the like are difficult to observe.

SUMMARY

To solve the above-described problems, the present embodiments provide the X-ray CT apparatus has: a determination unit configured to determine whether a radiographic image of a breast contains an implant part based on a pixel value distribution in a predetermined region concerning data of the radiographic image; a setting unit configured to change a setting of a parameter for a tone conversion process based on a determination made by the determination unit; a generating unit configured to generate a display image based on the radiographic image by application of the parameter; and a display unit configured to display the display image.

To solve the above-described problems, the present embodiments provide the image processing apparatus has: a determination unit configured to determine whether a radiographic image of a breast contains an implant part based on a pixel value distribution in a predetermined region concerning data of the radiographic image; a setting unit configured to change a setting of a parameter for a tone conversion process based on a determination made by the determination unit; and a generating unit configured to generate a display image based on the radiographic image by application of the parameter.

To solve the above-described problems, the present embodiments provide the image processing method has: determining whether a radiographic image of a breast contains an implant part based on a pixel value distribution in a predetermined region concerning data of the radiographic image; changing a setting of a parameter for a tone conversion process based on a determination made by the determination unit; and generating a display image based on the radiographic image by application of the parameter.

BRIEF DESCRIPTION OF THE DRAWINGS

In accompanying drawings.

DETAILED DESCRIPTION

A mammography apparatus according to present embodiments will be described with reference to the drawings.

Figure 1:
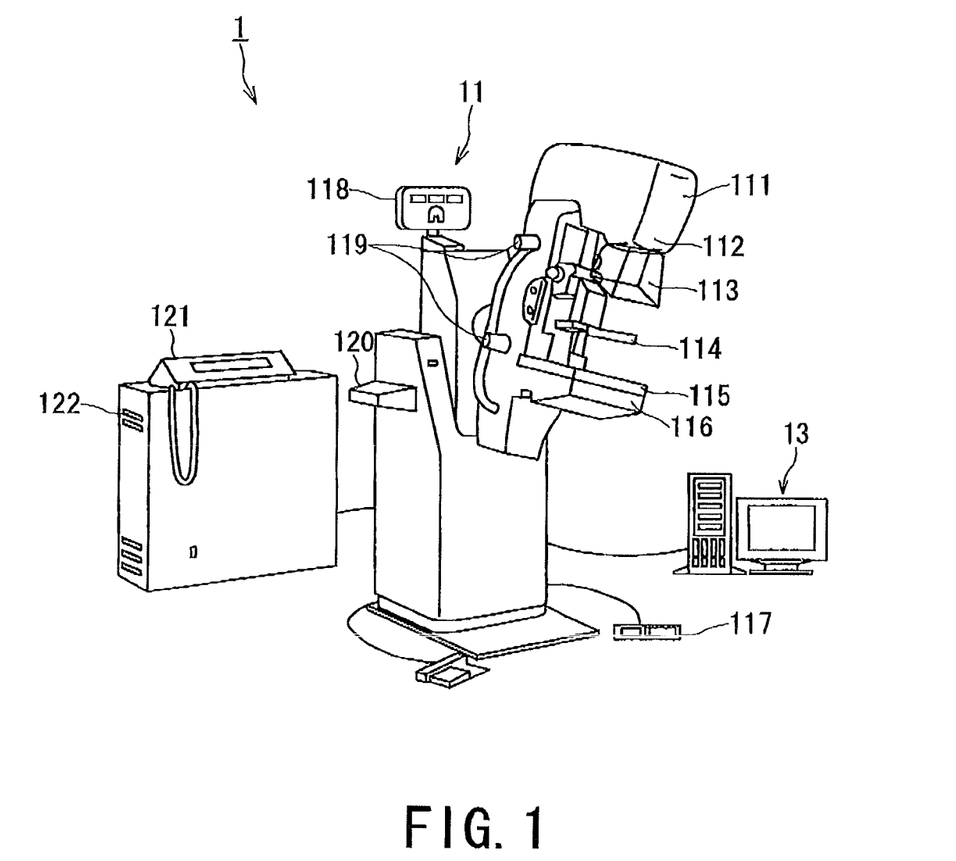
FIG. 1 is an external perspective view showing a structure of a mammography apparatus according to present embodiments.
Figure 2:
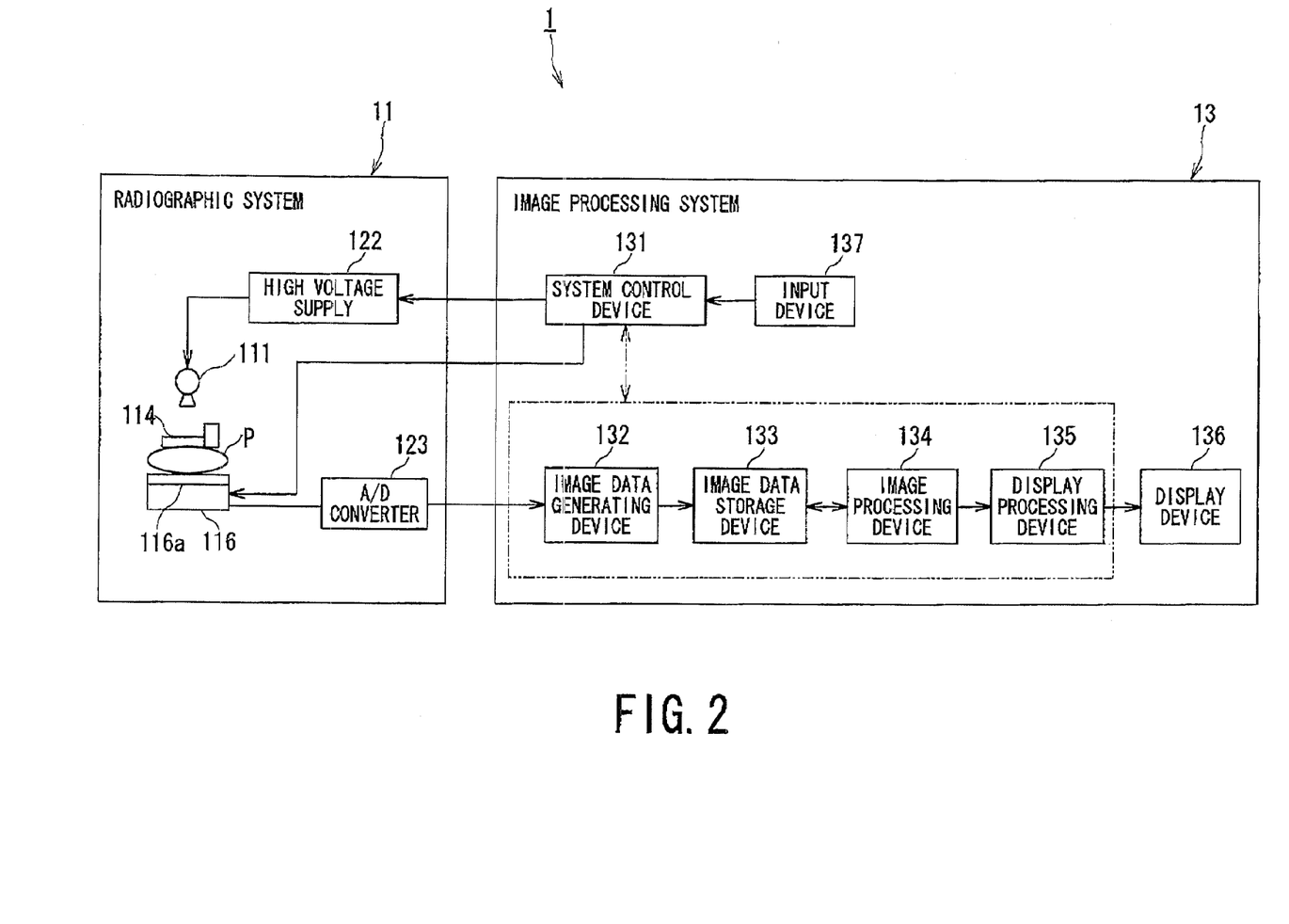
FIG. 2 is a block diagram showing a configuration of the mammography apparatus according to the present embodiments.

FIG. 1 is an external perspective view showing a structure of the mammography apparatus according to the present embodiments. FIG. 2 is a block diagram showing a configuration of the mammography apparatus according to the present embodiments.

FIGS. 1 and 2 show the mammographic X-ray apparatus (mammography apparatus) 1 according to the present embodiments which is capable of radiographing a breast of a patient P as an object. The mammography apparatus 1 includes a radiographic system 11 and an image processing system 13.

The radiographic system 11 includes an X-ray tube 111 as an X-ray source, a radiation quality adjustment filter/radiation field limiting mask 112, a face guard 113, a breast compression plate 114, a grid 115, a radiographic table 116, a compression foot pedal 117, an information display panel 118, a C-arm vertical-travel/rotation fine tuning switch 119, a side panel 120, a radiographic condition setting panel 121, a high voltage supply 122, and an A/D (analog-to-digital) converter 123.

The X-ray tube 111 is a vacuum tube designed to draw high voltage power from the high voltage supply 122 and emits an X-ray beam toward the radiographic table 116 through the breast of the patient P according to conditions of the high voltage power.

The radiation quality adjustment filter/radiation field limiting mask 112 is an adjustment device designed to adjust radiation quality of the X-ray beam generated by the X-ray tube 111 and limits a radiation field of the X-ray beam.

The face guard 113 is a protector designed to protect the head of the patient P from X-ray exposure during radiography.

The breast compression plate 114 is a compression device installed above the radiographic table 116 to compress the breast of the patient P against the radiographic table 116 during radiography. The breast compression plate 114 is made of a transparent resin and is supported in such a way as to be able to move close to or away from the radiographic table 116. By moving the breast compression plate 114 toward the radiographic table 116, it is possible to thinly compress the breast of the patient P into an approximately uniform thickness.

The grid 115 is a device designed to remove scattered rays and thereby improves a contrast of the radiographic image.

The radiographic table 116 contains an FPD (flat panel detector) 116a designed to detect the X-ray beam which has passed through the breast of the patient P. In the FPD 116a, multiple detector elements are arranged two-dimensionally, and scanning lines and signal lines are disposed orthogonally to each other among the detector elements.

The compression foot pedal 117 is designed to be pressed by an operator to adjust vertical position of the breast compression plate 114.

The information display panel 118 is designed to display various information including compression information.

The C-arm vertical-travel/rotation fine tuning switch 119 is used to rotate and vertically move a C arm which includes the X-ray tube 111 and radiographic table 116.

The side panel 120 is a control panel used to control various parts of the mammography apparatus 1.

The radiographic condition setting panel 121 is used to set conditions of X-ray radiography.

The high voltage supply 122 is designed to supply voltage to the X-ray tube 111.

The A/D converter 123 converts projection data which is a time-series analog signal (video signal) outputted from the FPD 116a into a digital signal and outputs the digital signal to the image processing system 13.

The X-ray beam generated by the X-ray tube 111 of the radiographic system 11 has its irradiation range narrowed by the radiation quality adjustment filter/radiation field limiting mask 112 and directed at the breast of the patient P compressed between the breast compression plate 114 and radiographic table 116. Then, the X-ray beam which has passed through the patient's breast is detected by the FPD 116a, converted into projection data, and outputted to the image processing system 13.

On the other hand, the image processing system 13 is designed to control operation of the entire mammography apparatus 1 and performs image processing on radiographic images acquired by the radiographic system 11. The image processing system 13 includes a system control device 131, an image data generating device 132, an image data storage device 133, an image processing device 134, a display processing device 135, a display device 136, and input devices 137.

The system control device 131 includes a CPU (central processing unit) and memory. In response to a command received as the operator operates the input devices 137 or received otherwise, the CPU controls operation of the radiographic system 11 or controls the entire image processing system 13.

Under the control of the system control device 131, the image data generating device 132 performs a logarithmic transformation process (LOG process) and, as required, an addition process, on the projection data transmitted from the A/D converter 123 of the radiographic system 11, thereby generates radiographic image data, and stores the radiographic image data in the image data storage device 133.

Under the control of the system control device 131, the image processing device 134 applies an enlargement/toning/space-filtering process, minimum-value/maximum-value tracing process, addition process, and the like to the radiographic image data to be stored in the image data storage device 133, where the minimum-value/maximum-value tracing process handles radiographic images accumulated in time sequence and the addition process is performed to remove noise. The radiographic image data subjected to image processing by the image processing device 134 is stored in the image data storage device 133.

The display processing device 135 generates display image data using parameters of an auto window function (tone conversion process) based on the radiographic images outputted from the system control device 131 or image processing device 134, adds character information of various parameters, a scale, and the like to the display images, and outputs the display images as a video signal to the display device 136.

The display device 136 displays the display images received from the display processing device 135, together with the character information of various parameters, the scale, and the like.

The input devices 137 include a keyboard, a mouse, and the like which can be operated by the operator. An input signal is sent to the system control device 131 according to the operation.

Incidentally, the mammography apparatus 1 according to the present embodiments as described herein radiographs the breast of the patient P in a sitting position, but this is not restrictive. For example, the mammography apparatus 1 may radiograph the breast of the patient P in a supine position.

Figure 3:
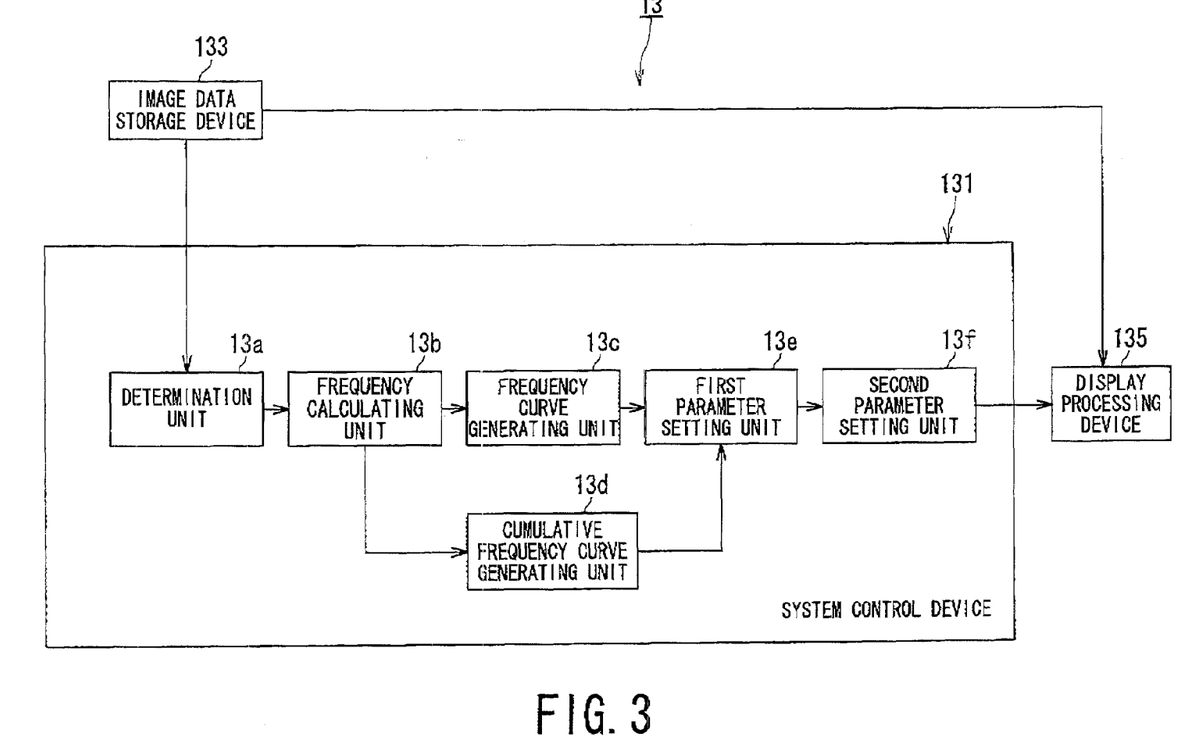
FIG. 3 is a block diagram showing functions of an image processing system of the mammography apparatus according to the present embodiments.

FIG. 3 is a block diagram showing functions of the image processing system 13 of the mammography apparatus 1.

As the CPU in the system control device 131 of the image processing system 13 executes a program, the system control device 131 functions as a determination unit 13a, a frequency calculating unit 13b, a frequency curve generating unit 13c, a cumulative frequency curve generating unit 13d, a first parameter setting unit 13e, and a second parameter setting unit 13f, as shown in FIG. 3. Incidentally, all or part of the units 13a to 13f of the system control device 131 may be provided as hardware in the system control device 131.

The determination unit 13a has a function of determining whether the radiographic image contains an implant part based on a pixel value distribution in a predetermined region included in the radiographic image data generated by the image processing device 134. Specifically, the determination unit 13a sets two pixel lows approximately parallel to a chest wall direction of the patient P and located near the chest wall using the radiographic image data by taking advantage of the fact that an implant such as a silicon pack, if exists, is located on the side of the chest wall and that position changes in the pixel values of the implant part in the radiographic image are smaller than position changes in the pixel values of a mammary gland area and the like and determines whether the radiographic image contains the implant part based on relationship between two profiles (positions/pixel value curves) corresponding to the two pixel lows. For example, the determination unit 13a calculates a differential profile based on the two profiles, calculates an amount of dispersion (standard deviation) in a range around the center of the differential profile, and determines that the radiographic image contains the implant part when the amount of dispersion is not above a threshold. Also, for example, when a correlation coefficient between required ranges around the center of the differential profile is above a threshold, the determination unit 13a determines that the radiographic image contains the implant part.

Figure 4:
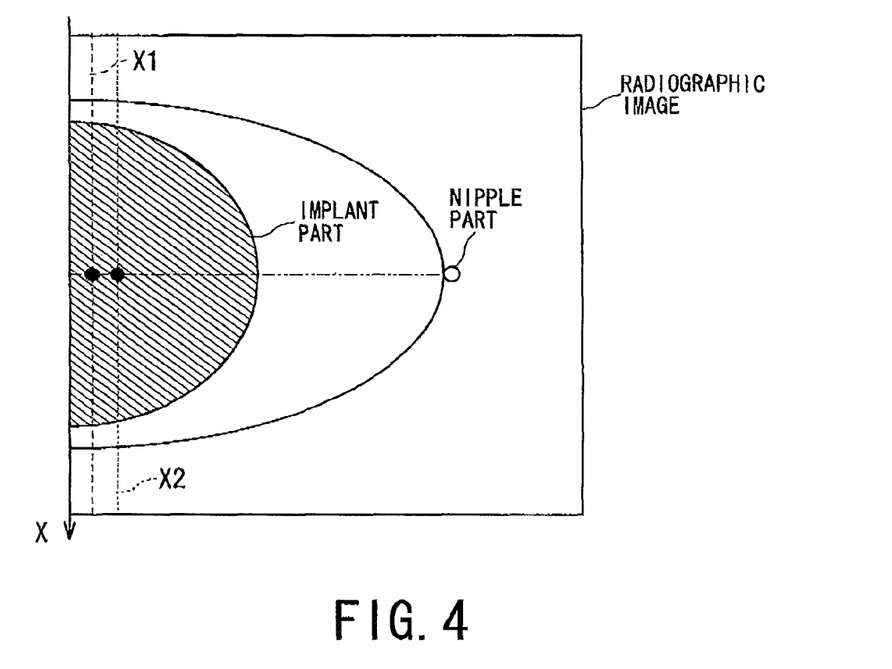
FIG. 4 is a schematic diagram showing an example of two pixel lows parallel to a chest wall direction of a patient.

FIG. 4 is a schematic diagram showing an example of two pixel lows parallel to the chest wall direction of the patient P.

As shown in FIG. 4, the determination unit 13a sets two pixel lows X1 and X2 approximately parallel to the direction X of the chest wall (e.g., direction of the pixel low which has the smallest total pixel value among pixel lows on four sides of an outer frame of the radiographic image) of the patient P and located near the chest wall (at least on the chest wall side of the center of the radiographic image). Preferably the two pixel lows X1 and X2 are spaced approximately 10 pixels apart so that changes in patterns of mammary gland area and the like in the radiographic image can be recognized.

Also, in FIG. 4, intersection points between a perpendicular line drawn from a nipple part to the chest wall and pixel lows X1 and X2 in the radiographic image are designated as the centers of respective profiles, where the nipple part has been extracted by a typical extraction method. However, the method for setting the centers of profiles is not limited to this. For example, intersection points between a perpendicular line drawn from the image center of the radiographic image to the chest wall and the pixel lows X1 and X2 may be designated as the centers of respective profiles.

Figure 5:
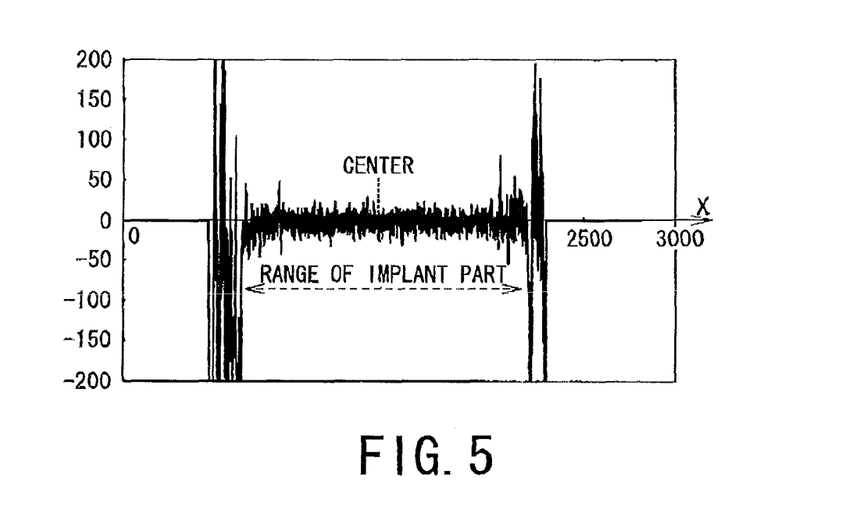
FIG. 5 is a diagram showing a first example of a differential profile.
Figure 6:
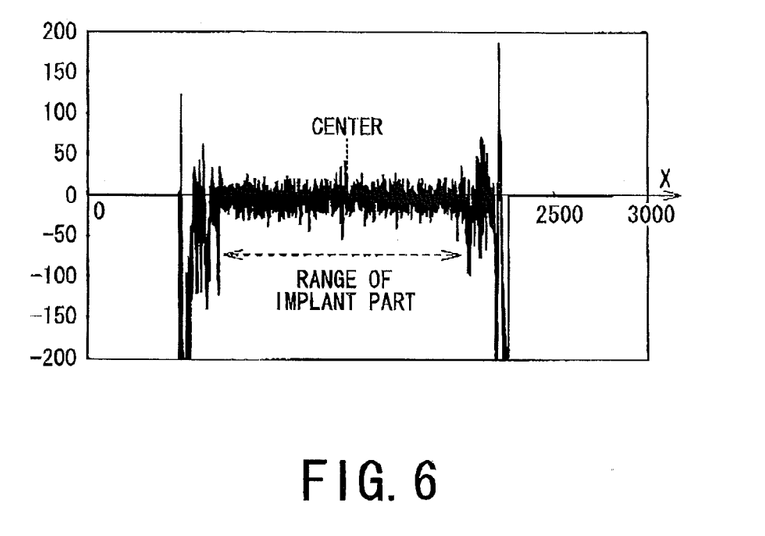
FIG. 6 is a diagram showing a second example of a differential profile.
Figure 7:
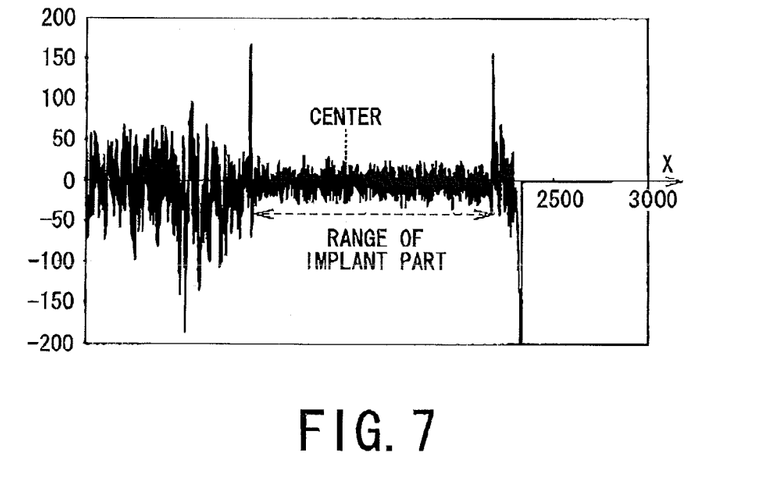
FIG. 7 is a diagram showing a third example of a differential profile.
Figure 8:
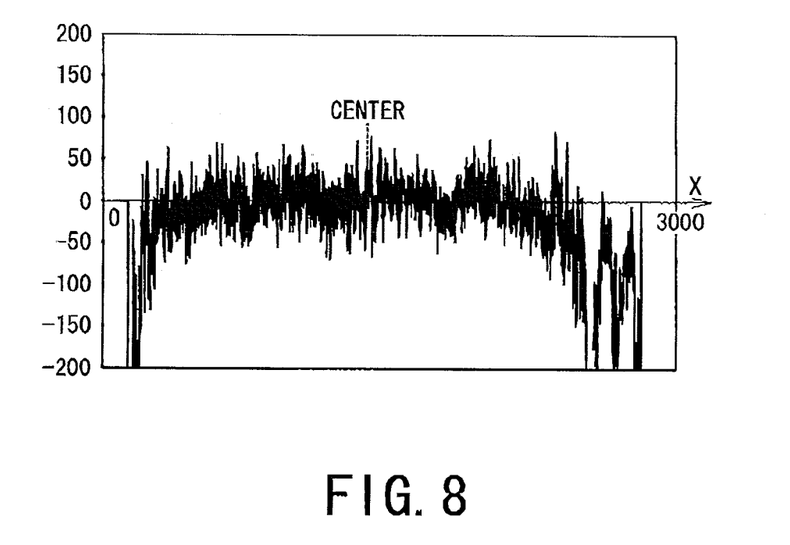
FIG. 8 is a diagram showing a fourth example of a differential profile.
Figure 9:
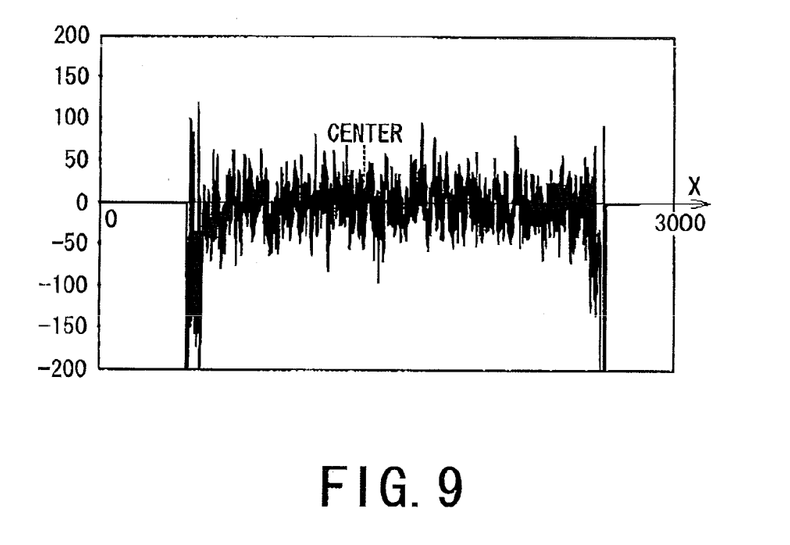
FIG. 9 is a diagram showing a fifth example of a differential profile.

FIGS. 5 to 9 are diagrams showing examples of differential profiles. FIG. 5 shows a first example of a differential profile related to a first patient P1 with the implant part in a radiographic image. FIG. 6 shows a second example of a differential profile related to a second patient. P2 with an implant part in a radiographic image. FIG. 7 shows a third example of a differential profile related to a third patient P3 with the implant part in a radiographic image. FIG. 8 shows a fourth example of a differential profile related to a fourth patient P4 without the implant part in a radiographic image. FIG. 9 shows a fifth example of a differential profile related to a fifth patient P5 without the implant part in a radiographic image.

In the differential profiles for the patients P1 to P3 shown in FIGS. 5 to 7 with the implant part in the radiographic images, decreases in amplitude are observed in a range containing the center of the chest wall direction X and corresponding to a range occupied by the implant part when compared to the differential profiles for the patients P4 and P5 shown in FIGS. 8 and 9 without the implant part in the radiographic images. This allows the determination unit 13a to determine whether the radiographic image contains the implant part using threshold processing based on a difference in the amount of amplitude dispersion in the range containing the center of the chest wall direction X. Incidentally, noise and sensitivity vary with the mammography apparatus 1 (system). Thus, preferably the threshold of standard deviation is set for each mammography apparatus 1.

In the above description given with reference to FIGS. 4 to 9, the determination unit 13a sets two pixel lows approximately parallel to the direction of the chest wall and located near the chest wall and determines whether the radiographic image contains the implant part based on the relationship between two profiles corresponding to the two pixel lows, but this is not restrictive. For example, the determination unit 13a may determine whether the radiographic image contains the implant part based on amounts of change in the pixel values on the perpendicular line drawn from the nipple part to the chest wall shown in FIG. 4.

The frequency calculating unit 13b shown in FIG. 3 has a function of finding the frequency of the pixel value of each pixel in the radiographic image stored in the image data storage device 133.

The frequency curve generating unit 13c has a function of generating a frequency distribution (histogram) based on the frequency of the pixel value of each pixel calculated by the frequency calculating unit 13b and generating a frequency curve smoothed based on the frequency distribution.

The cumulative frequency curve generating unit 13d has a function of generating a cumulative frequency distribution beginning with a low pixel value based on the frequency of the pixel value of each pixel calculated by the frequency calculating unit 13b and generating a cumulative frequency curve smoothed based on the cumulative frequency distribution.

The first parameter setting unit 13e has a function of changing a setting of a minimum pixel value based on the determination made by the determination unit 13a as to whether the radiographic image contains the implant part, where the minimum pixel value is used as a parameter of the auto window function. Specifically, when the determination unit 13a determines that the radiographic image contains the implant part, the first parameter setting unit 13e sets the minimum pixel value according to the present embodiments to a pixel value larger than the conventional minimum pixel value at which the cumulative frequency curve generated by the cumulative frequency curve generating unit 13d starting from the low-pixel-value side reaches a predetermined threshold (e.g., 10% of the total). On the other hand, when the determination unit 13a determines that the radiographic image does not contain the implant part, the first parameter setting unit 13e sets the minimum pixel value to the value at which the cumulative frequency curve generated by the cumulative frequency curve generating unit 13d starting from the low-pixel-value side reaches a predetermined threshold (e.g., 10% of the total), as is conventionally the case. That is, the first parameter setting unit 13e sets a different minimum pixel value depending on whether or not the radiographic image contains the implant part.

Also, regardless of the determination made by the determination unit 13a, the first parameter setting unit 13e sets a maximum pixel value for use as a parameter of the auto window function by excluding a maximum pixel value of the radiographic image or a background area of the radiographic image. That is, by setting the maximum pixel Value and minimum pixel value as parameters of the auto window function, the first, parameter setting unit 13e can determine a window width.

Preferably, the first parameter setting unit 13e finds, on the cumulative frequency curve, the cumulative frequency at the pixel value which corresponds to a peak on the side of the lowest pixel value on the frequency curve generated by the frequency curve generating unit 13c, finds the pixel value which corresponds to double the cumulative frequency thus found on the cumulative frequency curve, and adopts the pixel value thus found, as the minimum pixel value. The reason why the pixel value which corresponds to double the cumulative frequency at the pixel value which corresponds to the peak is preferable as the minimum pixel value is that an impact of a hill which contains the peak and represents the implant part can be eliminated almost completely. That is, by doubling the cumulative frequency from the start point (end on the low-pixel-value side) of the hill to the peak, the impact of the hill from the start point through the peak to the end point (end on the high-pixel-value side) can be eliminated almost completely. Incidentally, although the pixel value which corresponds to double the cumulative frequency at the pixel value which corresponds to the peak is set as the minimum pixel value, this is not restrictive.

Figure 10:
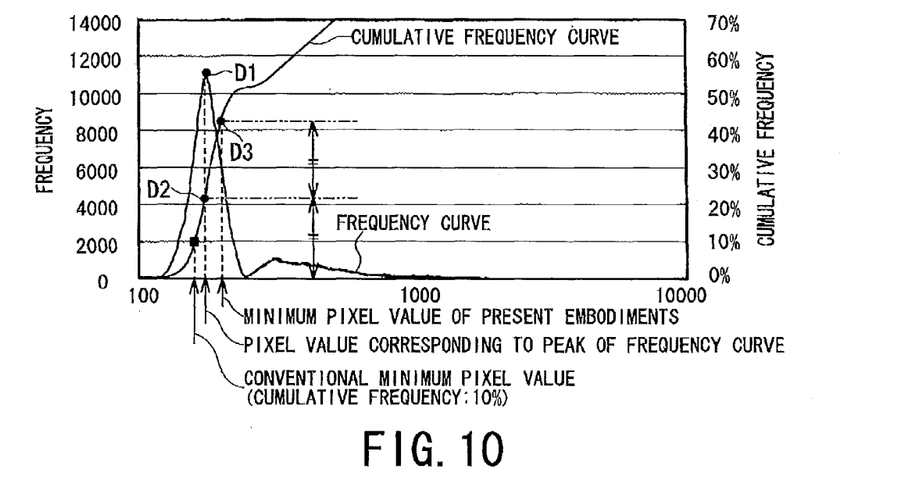
FIG. 10 is a diagram for illustrating a method for setting a minimum pixel value in the first example of the differential profile shown in FIG. 5.
Figure 11:
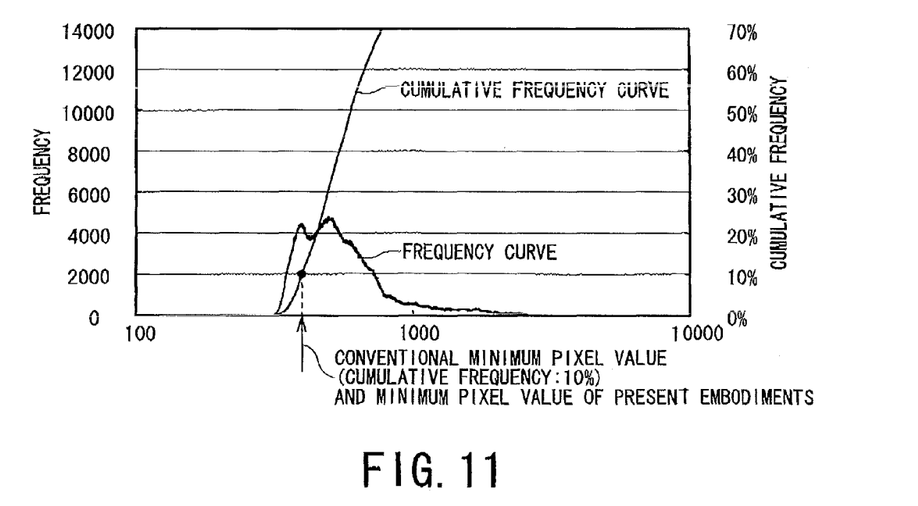
FIG. 11 is a diagram for illustrating a method for setting a minimum pixel value in the fourth example of the differential profile shown in FIG. 8.

FIG. 10 is a diagram for illustrating a method for setting the minimum pixel value in the first example of the differential profile shown in FIG. 5. FIG. 11 is a diagram for illustrating a method for setting the minimum pixel value in the fourth example of the differential profile shown in FIG. 8.

As shown in FIG. 10, if the radiographic image contains the implant part, the first parameter setting unit 13e finds the peak D1 on the side of the lowest pixel value on the frequency curve. The first parameter setting unit 13e finds, on the cumulative frequency curve, the cumulative frequency (point D2) at the pixel value which corresponds to the peak D1. The first parameter setting unit 13e finds the pixel value which corresponds to the cumulative frequency (point D3) which is double the cumulative frequency at point D2 on the cumulative frequency curve. Then, the first parameter setting unit 13e designates the pixel value at point D3 as the minimum pixel value. On the other hand, with conventional mammography apparatus, even if a radiographic image contains the implant part, the pixel value at which a cumulative frequency curve reaches 10% of the total is set as a minimum pixel value.

As shown in FIG. 11, if the radiographic image does not contain the implant part, the first parameter setting unit 13e sets the minimum pixel value to the value at which the cumulative frequency curve reaches a predetermined threshold (e.g., 10% of the total), as is conventionally the case.

The second parameter setting unit 13f shown in FIG. 3 has a function of setting a center pixel value between the maximum pixel value and the minimum pixel value generated by the first parameter setting unit 13e, as a window level which is a parameter of the auto window function.

Using the auto window function which is based on the maximum pixel value and the minimum pixel value set by the first parameter setting unit 13e as well as on the window level set by the second parameter setting unit 13f, the display processing device 135 generates a display image from the radiographic image outputted from the image processing device 134 and outputs the display image to the display device 136.

Figure 12:
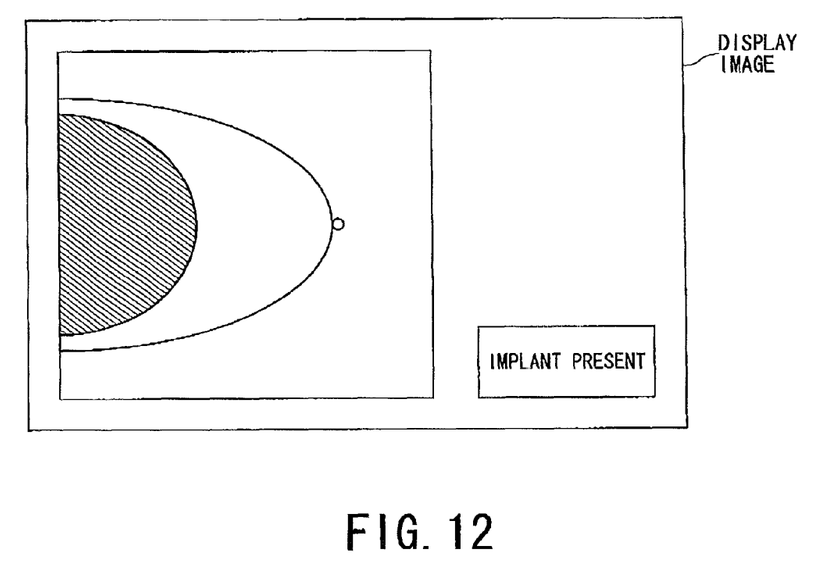
FIG. 12 is a diagram showing an example of a display image displayed on a display device.

FIG. 12 is a diagram showing an example of a display image displayed on the display device 136.

FIG. 12 shows a display image generated using the parameters of the auto window function set by the first parameter setting unit 13e and the second parameter setting unit 13f. When the determination unit 13a determines that the radiographic image contains the implant part, the display processing device 135 outputs the display image containing "implant present" information to the display device 136, as shown in FIG. 12. On the other hand, when the determination unit 13a determines that the radiographic image does not contain the implant part, the display processing device 135 outputs the display image containing "no implant present" information to the display device 136 although not illustrated.

If the mammography apparatus 1 has capability for tomosynthesis of the breast of the patient P, parameters of the auto window function may be set by performing the processes of the determination unit 13a to the second parameter setting unit 13f (described above) on only one radiographic image out of multiple radiographic images obtained by multiple angles (views) and then multiple display images may be generated from all the radiographic images using the auto window function based on the set parameters. Also, when the mammography apparatus 1 has capability for tomosynthesis of the breast of the patient P, the parameters of the auto window function may be set by performing the processes of the determination unit 13a to the second parameter setting unit 13f (described above) on radiographic images generated from multiple radiographic images obtained by multiple angles.

Even if the radiographic image contains the implant part, the mammography apparatus 1 according to the present embodiments is able to set parameters of the auto window function suitable for the breast examination based on the radiographic image, and generate and display the display image based on the set parameters.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fail within the scope and spirit of the inventions.

What is claimed is:

1. A mammography apparatus, comprising a processing circuit configured to:
   determine whether a breast region of a radiographic image including a breast therein contains an implant part or not on a basis of a pixel value distribution in a predetermined region concerning data of the radiographic image;

set, when it is determined that the breast region therein contains the implant part, a minimum pixel value in a tone conversion process, the minimum pixel value being larger than a pixel value of the implant part; and display the radiographic image as a display image adapted in accordance with the set minimum pixel value and a maximum pixel value in the tone conversation process.

2. The mammography apparatus according to claim 1, wherein the processing circuit is configured to:

set a plurality of pixel lows which is approximately parallel to a pixel low containing the chest wall in the radiographic image and is located on the chest wall side from a center of the radiographic image; and determine whether or not the breast region therein contains the implant part on a basis of a relationship among a plurality of profiles corresponding to the plurality of pixel lows as a plurality of pixel value distributions.

3. The mammography apparatus according to claim 2, wherein the processing circuit is configured to:

generate a differential profile on a basis of the plurality of profiles, which specifically is two in number;

calculate an amount of dispersion in a required range around a center of the differential profile; and determine that the breast region therein contains the implant part when the amount of dispersion is not above a threshold.

4. The mammography apparatus according to claim 2, wherein the processing circuit is configured to determine, on a basis of two profiles which is the plurality of profiles, that the breast region therein contains the implant part when a correlation coefficient between required ranges around centers of the profiles is above a threshold.

5. The mammography apparatus according to claim 1, wherein the processing circuit is configured to calculate a frequency of a pixel value of each pixel in the radiographic image.

6. The mammography apparatus according to claim 5, wherein the processing circuit is configured to find a peak on the side of the lowest pixel value on a distribution of the frequency and sets the minimum pixel value to a pixel value which corresponds to double a cumulative frequency at a pixel value which corresponds to the peak.

7. The mammography apparatus according to claim 6, wherein the processing circuit is configured to find the peak based on a frequency curve obtained by smoothing the distribution of the frequency and sets the minimum pixel value based on a cumulative frequency curve obtained by smoothing a distribution of the cumulative frequency.

8. The mammography apparatus according to claim 1, wherein the processing circuit is configured to set a center pixel value between the maximum pixel value and the minimum pixel value as a window level.

9. An image processing apparatus, comprising a processing circuit configured to:

determine whether a breast region of a radiographic image including a breast therein contains an implant part or not on a basis of a pixel value distribution in a predetermined region concerning data of the radiographic image;

set, when it is determined that the breast region therein contains the implant part, a minimum pixel value in a tone conversion process, the minimum pixel value being larger than a pixel value of the implant part; and display the radiographic image as a display image adapted in accordance with the set minimum pixel value and a maximum pixel value in the tone conversation process.

10. The image processing apparatus according to claim 9, wherein the processing circuit is configured to:

set a plurality of pixel lows which is approximately parallel to a pixel low containing the chest wall in the radiographic image and is located on the chest wall side from a center of the radiographic image; and determine whether or not the breast region therein contains the implant part on a basis of a relationship among a plurality of profiles corresponding to the plurality of pixel lows as a plurality of pixel value distributions.

11. The image processing apparatus according to claim 10, wherein the processing circuit is configured to:

generate a differential profile on a basis of the plurality of profiles, which specifically is two in number:

calculate an amount of dispersion in a required range around a center of the differential profile; and determine that the breast region therein contains the implant part when the amount of dispersion is not above a threshold.

12. The image processing apparatus according to claim 10, wherein the processing circuit is configured to determine, on a basis of two profiles which is the plurality of profiles, that the breast region therein contains the implant part when a correlation coefficient between required ranges around centers of the profiles is above a threshold.

13. The image processing apparatus according to claim 9, wherein the processing circuit is configured to calculate a frequency of a pixel value of each pixel in the radiographic image.

14. The image processing apparatus according to claim 13, wherein the processing circuit is configured to find a peak on the side of the lowest pixel value on a distribution of the frequency and sets the minimum pixel value to a pixel value which corresponds to double a cumulative frequency at a pixel value which corresponds to the peak.

15. The image processing apparatus according to claim 14, wherein the processing circuit is configured to find the peak based on a frequency curve obtained by smoothing the distribution of the frequency and is configured to set the minimum pixel value based on a cumulative frequency curve obtained by smoothing a distribution of the cumulative frequency.

16. The mammography apparatus according to claim 9, wherein the processing circuit is configured to set a center pixel value between the maximum pixel value and the minimum pixel value as a window level.

17. An image processing method, comprising:

generating a radiographic image using a mammography device;

determining by using a processing circuit whether a breast region of a radiographic image including a breast therein contains an implant part or not on a basis of a pixel value distribution in a predetermined region concerning data of the radiographic image;

setting by using the processing circuit, when it is determined that the breast region therein contains the implant part, a minimum pixel value in a tone conversion process, the minimum pixel value being larger than a pixel value of the implant part; and displaying the radiographic image on a display device as a display image adapted in accordance with the set minimum pixel value and a maximum pixel value in the tone conversation process.

\* \* \* \* \*